United States Patent
Kitagawa

[11] Patent Number: 5,391,988
[45] Date of Patent: Feb. 21, 1995

[54] METHOD AND APPARATUS FOR DETECTING FLAWS WITHIN A CONDUCTIVE OBJECT WHILE CANCELLING THE EFFECTS OF VARIATION IN DISTANCE BETWEEN THE DETECTION APPARATUS AND THE CONDUCTIVE OBJECT

[75] Inventor: Shigeru Kitagawa, Kurashiki, Japan

[73] Assignees: Kabushiki Kaisha Nihon Hihakai Keisoku Kenkyusho, Kurashiki; Mitsui Engineering & Shipbuilding Co., Ltd., Tokyo; MES Testing & Research Center Co., Ltd., Tamano, all of Japan

[21] Appl. No.: 39,234

[22] PCT Filed: Sep. 13, 1991

[86] PCT No.: PCT/JP91/01218
    § 371 Date: Apr. 20, 1993
    § 102(e) Date: Apr. 20, 1993

[87] PCT Pub. No.: WO93/06477
    PCT Pub. Date: Apr. 1, 1993

[51] Int. Cl.6 ............................................. G01N 27/90
[52] U.S. Cl. ....................................... 324/225; 324/233; 324/240
[58] Field of Search .......... 324/225, 228, 235, 239–242

[56] References Cited

U.S. PATENT DOCUMENTS

| | | | |
|---|---|---|---|
| 3,580,056 | 5/1971 | Warner | 324/240 X |
| 3,707,672 | 12/1972 | Miller et al. | 324/239 |
| 4,117,403 | 9/1978 | Forster et al. | 324/240 |
| 4,644,271 | 2/1987 | Toth et al. | 324/228 X |
| 4,954,778 | 9/1990 | Champonnois et al. | 324/233 |
| 5,059,902 | 10/1991 | Linder | 324/239 X |

FOREIGN PATENT DOCUMENTS

| | | |
|---|---|---|
| 57-96254 | 6/1982 | Japan . |
| 60-146147 | 8/1985 | Japan . |
| 62-85857 | 4/1987 | Japan . |

*Primary Examiner*—Gerard R. Strecker
*Attorney, Agent, or Firm*—Armstrong, Westerman, Hattori, McLeland & Naughton

[57] ABSTRACT

A method and apparatus for nondestructively detecting a flaw such as a hairline crack or defect within a conductive object to be inspected. Surface flaws can be distinguished from deep flaws. The pulse duration of the pulse voltage induced in the secondary coil of a sensor is measured at two separate time instances. At one time instance, the pulse duration is affected by variations in the distance between the sensor and the object but is not affected by the flaw. At the other time instance the pulse duration is affected by said variations and also by the flaw. The effect of said variations is cancelled, using these two measured pulse durations. Only a signal correctly indicating the flaw is extracted to detect the presence of the flaw.

10 Claims, 11 Drawing Sheets

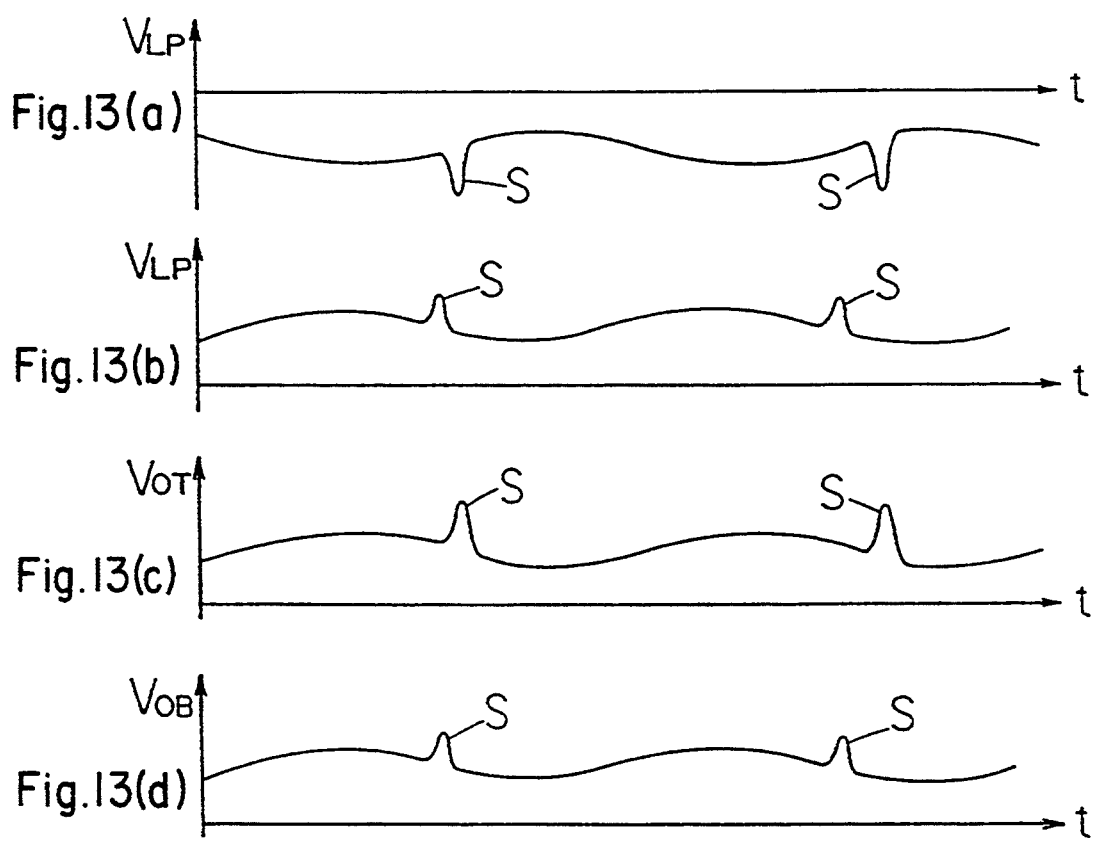

METHOD AND APPARATUS FOR DETECTING FLAWS WITHIN A CONDUCTIVE OBJECT WHILE CANCELLING THE EFFECTS OF VARIATION IN DISTANCE BETWEEN THE DETECTION APPARATUS AND THE CONDUCTIVE OBJECT

FIELD OF THE INVENTION

The present invention relates to a method and apparatus for nondestructively detecting flaws such as hairline cracks and defects within a conductive object undergoing testing and, more particularly, to method and apparatus capable of distinguishing surface flaws from internal, deep flaws.

BACKGROUND OF THE INVENTION

There is a related art apparatus for detecting flaws such as hairline cracks and defects or the kind of material of a test object using a sensor comprising a ferrite core on which primary and secondary coils are wound. This sensor is moved while being kept in contact with the surface of the conductive test object. A rectangular-wave current is supplied to the primary coil to induce eddy currents in a minute region on the surface of the inspected object. The eddy currents induce a magnetic field, which is detected by the secondary coil. The pulse duration of the voltage pulses detected by the secondary coil are measured. In this way, the flaws or the kind of material is detected. The principle of this detection utilizes the fact that the attenuation time of the eddy currents induced on the surface of the test object, i.e., the pulse duration, differs depending on the flaws such as hairline cracks or defects and on the kind of material.

The peak value and the pulse duration of the voltage pulse detected by the secondary coil are affected greatly by variations in the distance between the test object and the sensor. This makes it impossible to discern the sensor output signals indicating the flaws such as hairline cracks or defects and the material. Hence, the reliability of detection of flaws has presented problems.

Accordingly, it has been important for the flaw detection method and apparatus of this kind to reduce the effect of the aforementioned variations in the distance between the sensor and the object. For this purpose, various contrivances have been made. One example has been proposed by the present Applicant and is disclosed in Japanese Patent Laid-Open No. 316655/1989. In particular, the secondary coil output signal produces positive and negative driving currents in response to signal variations caused by variations in the distance between the sensor and the object. The driving currents activate driving coils disposed around a permanent magnet which is connected to one end of the sensor. In this manner, the distance between the sensor and the object is kept constant. However, the above-described driving currents must be supplied constantly. Also, large amounts of current must be supplied. Consequently, a large amount of electric power is consumed. In addition, the apparatus lacks portability. Furthermore, the responsiveness is a problem.

SUMMARY OF THE INVENTION

It is an object of the present invention to provide a flaw detection method and apparatus using eddy currents which cancel the effect of variations in the distance between a sensor including primary and secondary coils and an object undergoing testing only by analyzing the signal of the voltage pulse induced in the secondary coil while directly using the prior art principle employing the attenuation characteristics of eddy currents without mechanically varying the sensor, whereby only the flaws, such as hairline cracks and defects within the object, are detected correctly.

A flaw detection method using eddy currents according to a first embodiment of the invention uses a ferrite core on which primary and secondary coils are wound. A rectangular-wave current is supplied to the primary coil to induce a voltage pulse in the secondary coil. The pulse duration of the induced voltage pulse is measured at two separate time instances corresponding to two different threshold voltages. The effect of the variations in the distance between the ferrite core and the conductive test object is canceled, using both pulse durations. As a result, only correct flaws such as hairline cracks or defects within the object are detected.

Threshold voltages used for measurement of the pulse duration of the pulse voltage induced in the secondary coil are set to first and second voltages, respectively. The first voltage is affected by variations in the distance between the front end of the ferrite core and the object under inspection but is not affected by flaws such as hairline cracks and defects within the object. The second voltage is affected by the variations in the distance between the front end of the ferrite core and the object and also by flaws such as hairline cracks and defects within the object. A signal proportional to the difference between both pulse durations is obtained.

A flaw detection apparatus according to a second embodiment of the invention comprises: a sensor consisting of a ferrite core on which primary and secondary coils are wound; a current pulse generator circuit for supplying a rectangular-wave current to the primary coil; a first comparator producing a rectangular-wave voltage having the same pulse duration as that portion of the voltage pulse induced in the secondary coil corresponding to a first threshold voltage; a second comparator producing a rectangular-wave voltage having the same pulse duration as that portion of the voltage pulse induced in the secondary coil corresponding to a second threshold voltage; two smoothing circuits which smooth the output signals from the first and second comparators, respectively, and convert them into DC voltages proportional to the pulse durations of the rectangular-wave voltages; and a canceling circuit which takes the difference between the output voltages from the smoothing circuits and produces a DC voltage signal that is unaffected by variations in the distance between the front end of the sensor and the object. The first threshold voltage is set such that the pulse duration is increased or reduced, depending on variations in the distance between the front end of the sensor and the conductive object but is not affected by flaws such as hairline cracks and defects within the object. The second threshold voltage is set such that the pulse duration is increased or reduced, depending on the variations in the distance between the front end of the sensor and the conductive object to be inspected and is affected by flaws such as hairline cracks and defects within the object.

A flaw detection apparatus according to a third embodiment of the invention is similar to the second embodiment except that the smoothing circuits and the canceling circuit are replaced by a pulse generator circuit and a signal converter circuit. The pulse generator circuit produces a rectangular-wave voltage having a pulse duration equal to the difference between the pulse durations of the output voltages from the comparators. The signal converter circuit produces a DC voltage signal or a digital signal which is proportional to the pulse duration of the output voltage from the pulse generator circuit.

A flaw detection apparatus according to a fourth embodiment of the invention is similar to the second embodiment except that the canceling circuit is replaced by a different canceling circuit in which the DC voltages delivered from the smoothing circuits are each divided into two portions. This canceling circuit comprises first and second differential amplifiers and a potentiometer having a resistor and a slider. One portion of the DC voltage from the first smoothing circuit is applied directly to the first differential amplifier, while the other portion is applied via a first analog memory to the first differential amplifier. One portion of the DC voltage from the second smoothing circuit is applied directly to the second differential amplifier, whereas the other portion is applied via a second analog memory to the second differential amplifier. Each analog memory stores its input voltage and produces the stored voltage. The outputs from the differential amplifiers are applied across opposite ends of the resistor of the potentiometer. A DC voltage signal is obtained from the slider.

A flaw detection apparatus according to a fifth embodiment of the invention is similar to the fourth embodiment except that a low-pass filter and a differentiator circuit are added. The low-pass filter removes high-frequency noise superimposed on the DC voltage signal delivered from the canceling circuit. The differentiator circuit removes the low-frequency component superimposed on the DC voltage signal and detects only signals clearly indicating flaws.

A flaw detection apparatus according to a sixth embodiment of the invention is similar to the fourth embodiment except that a low-pass filter and a decision circuit are added. The low-pass filter removes high-frequency noise superimposed on the DC voltage signal delivered from the canceling circuit. The decision circuit discriminates surface flaws within the object to be inspected from deep flaws and produces signals indicating flaws to different terminals.

This decision circuit comprises a surface flaw detection circuit and a deep flaw detection circuit. The surface flaw detection circuit consists of a series combination of an inverting amplifier and a forwardly biased diode. The deep flaw detection circuit consists of a series combination of a non-inverting amplifier and a forwardly biased diode. A pair of comparators having a threshold voltage capable of removing low-frequency components are connected with opposite output terminals of the decision circuit. The comparators produce signals indicating flaws. A pair of lamps are connected with the output terminals of the comparators. The lamps are lit up when the signals indicating flaws are produced.

In the novel flaw detection method and apparatus described above, a pulse voltage is induced in the secondary coil by supplying a rectangular-wave current to the primary coil. When one end of this coil is brought close to the conductive object to be inspected, the pulse duration of the induced voltage pulse increases or decreases as a whole. The coil is moved along the surface of the object and passed over a flaw such as a hairline crack or defect. At this time, only the trailing portion of the pulse voltage varies. Utilizing this variation, the variations in the pulse duration due to variations in the distance between the coil and the object are canceled. Only the changes in the pulse duration due to a flaw such as a hairline crack or defect are detected in the form of signals.

More specifically, the pulse duration of the voltage pulse induced in the secondary coil is measured at two separate time instances. At one time instance, the pulse duration is affected by variations in the distance between the sensor and the object but is not affected by the flaw. At the other time instance, the pulse duration is affected by said variations and also by the flaw. The effect of said variations is canceled, using these two measured pulse durations. Only a signal correctly indicating the flaw is extracted to detect the presence.

Other and further objects of the invention will become obvious upon an understanding of the illustrative embodiments about to be described or will be indicated in the appended claims, and various advantages not referred to herein will occur to one skilled in the art upon employment of the invention in practice.

BRIEF DESCRIPTION OF THE DRAWINGS

FIGS. 13(a-d) represent a time chart showing signals produced from a decision circuit incorporated in the apparatus shown in FIG. 10, some of the signals indicating surface flaws, the others indicating deep flaws.

DETAILED DESCRIPTION OF THE INVENTION

Figure 1:
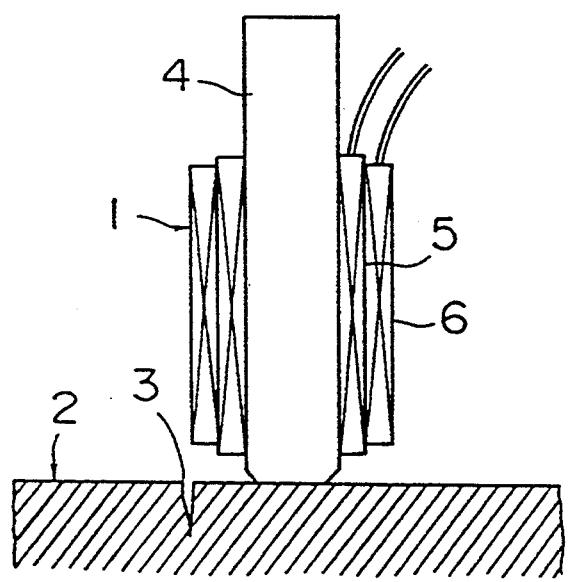
FIG. 1 is a schematic cross section of a sensor used in flaw detection according to the invention, and in which the sensor is placed on an object to be inspected.

Referring to FIG. 1, there are shown a sensor 1 according to the invention and an object 2 to be inspected. The sensor 1 is moved while kept in contact with the surface of the object 2 to detect a flaw 3 such as a hairline crack or defect within the object.

The sensor 1 comprises a ferrite core 4 on which a primary coil 5 and a secondary coil 6 are wound. The primary coil 5 is used for excitation. The secondary coil 6 is employed for detection. The ferrite core 4 can be replaced by any other member as long as it can concentrate magnetic flux in the same way as the core 4. The coils 5 and 6 may be wound either in the same direction or in opposite directions. The polarity of the output voltage from the secondary coil 6 is set according to signal processing performed later.

Figure 2:
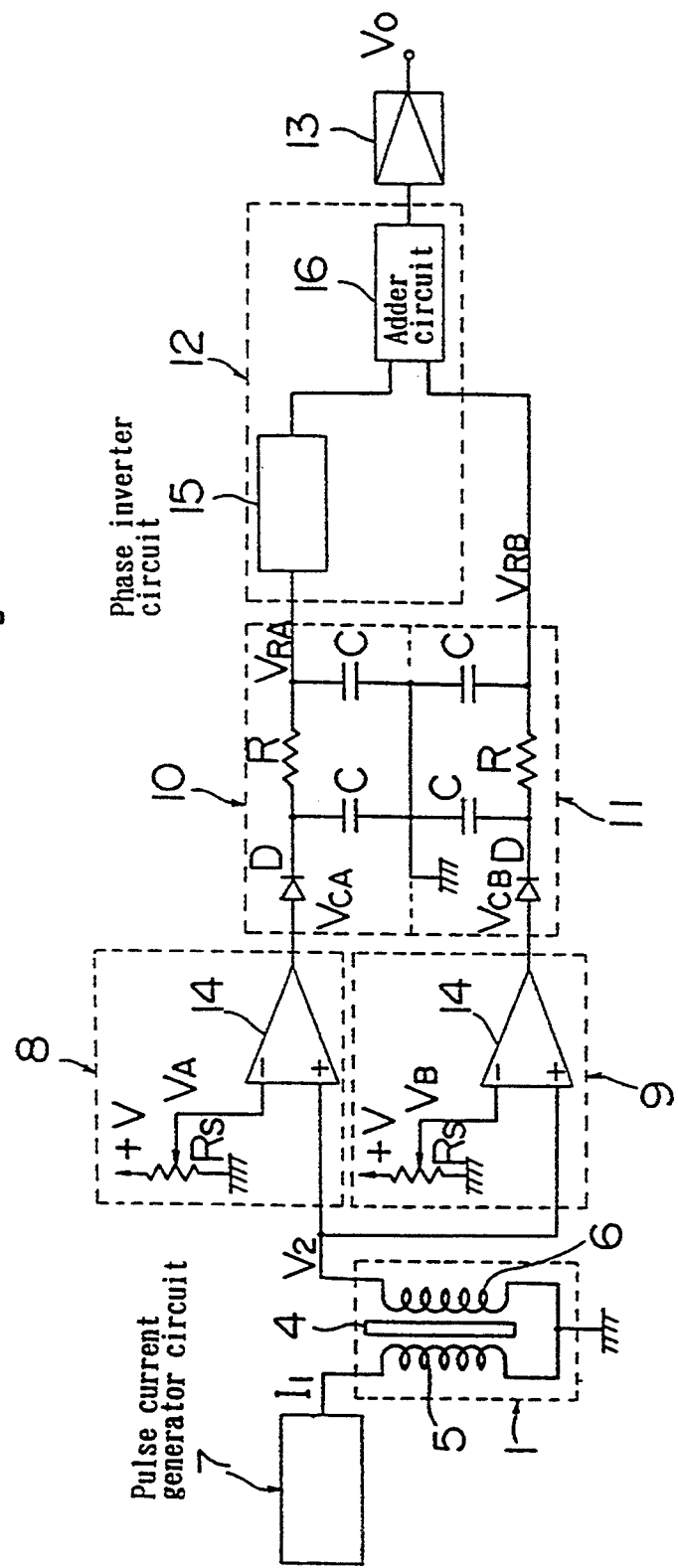
FIG. 2 is a schematic circuit diagram of a flaw detection apparatus according to the invention.

Referring next to FIG. 2, there is shown a flaw detection apparatus according to the invention. This apparatus comprises the sensor 1 described above, a pulse current generator circuit 7 supplying a rectangular-wave current $I_1$ to the primary coil 5 of the sensor 1, a first comparator 8, a second comparator 9, a smoothing circuit 10 for smoothing the output from the first comparator 8, a second smoothing circuit 11 for smoothing the output from the second comparator 9, and a canceling circuit 12 for canceling the effect of variations in the distance between the front end of the sensor 1 and the object 2 according to the output voltages from the smoothing circuits 10 and 11. The first comparator 8 produces a rectangular-wave voltage $V_{CA}$ having a pulse duration equal to the time period in which the pulse voltage $V_2$ induced in the secondary coil 6 is greater than a threshold voltage $V_A$. The second comparator 9 produces a rectangular-wave voltage $V_{CB}$ having a pulse duration equal to the time period in which the pulse voltage $V_2$ induced in the secondary coil 6 is greater than another threshold voltage $V_B$. An amplifier circuit 13 is connected to the output of the canceling circuit 12 to amplify the output from the canceling circuit 12 to an appropriate level. In this way, a desired voltage signal $V_0$ is produced from the amplifier circuit 13.

Figure 3:
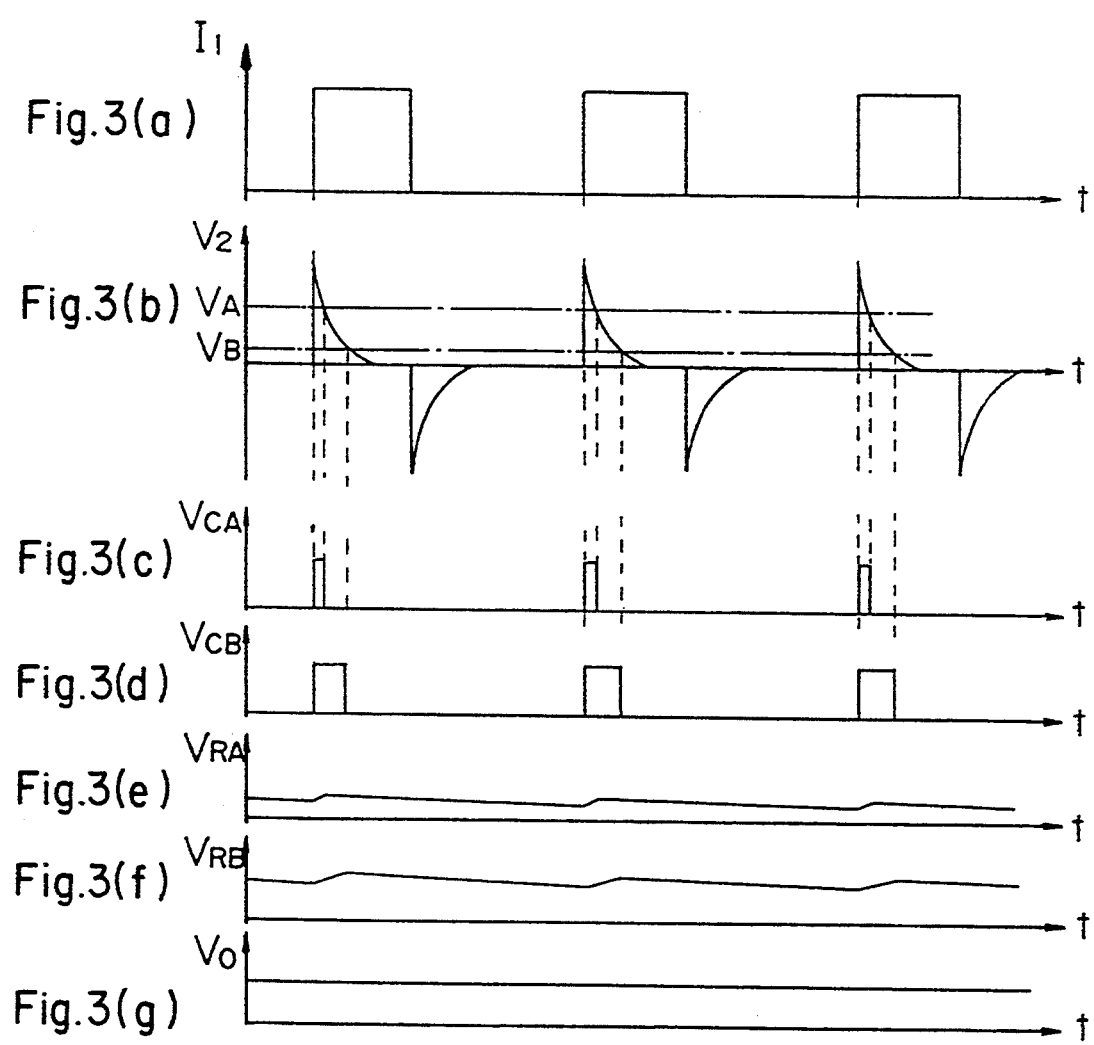
FIGS. 3(a-g) represent a time chart showing the waveforms produced at main portions of the circuit shown in FIG. 2.

The pulse current generator circuit 7 produces the rectangular-wave current $I_1$ as shown in FIG. 3. In the present embodiment, the frequency and the pulse duration of the rectangular-wave current $I_1$ are set to about 1 kHz and about 0.2 ms, respectively. This current is supplied to the primary coil 5 to apply a varying magnetic field substantially perpendicular to the surface of the object 2 under inspection. At the leading edge and the trailing edge of the current $I_1$, the pulse voltage $V_2$ having a pulse duration whose half-width value is about 10 μs is induced in the secondary coil 6.

Different threshold voltages of the voltage pulse $V_2$ are set into the first comparator 8 and the second comparator 9, respectively. As shown in FIGS. 3(c-d), the comparators 8 and 9 produce rectangular-wave voltages $V_{CA}$ and $V_{CB}$, respectively, having pulse durations equal to time periods in which voltage pulse $V_2$ is greater than threshold voltages $V_A$ and $V_B$, respectively. More specifically, the first comparator 8 has a first high-speed operational amplifier 14. The voltage pulse $V_2$ from the secondary coil 6 is applied to the positive terminal of the operational amplifier 14, while the threshold voltage $V_A$ is applied to the negative terminal, the threshold voltage $V_A$ being divided by a variable resistor $R_s$ across which a positive voltage $+V$ is applied. The second comparator 9 is similar in structure to the first comparator 8.except that the threshold voltage $V_B$ is applied through a second variable resistor $R_s$. The rectangular-wave voltages $V_{CA}$ and $V_{CB}$ have a given period and the same peak value but differ only in pulse duration.

The smoothing circuits 10 and 11 are each an ordinary rectifier circuit consisting of a diode D, a capacitor C, and a resistor R for removing negative spikes from the output from the corresponding comparator. The rectangular-wave voltages $V_{CA}$ and $V_{CB}$ are rectified and converted into DC voltages $V_{RA}$ and $V_{RB}$, respectively, proportional to the pulse durations of the rectangular-wave voltages $V_{CA}$ and $V_{CB}$ by the smoothing circuits 10 and 11, respectively. In FIGS. 3(e-f), the DC voltages $V_{RA}$ and $V_{RB}$ are shown to undulate, for illustrating the manner in which electrical charging and discharging are done by the capacitor C and the resistor R. In practice, these DC voltages are smoother.

The canceling circuit 12 is an analog circuit that produces the difference between the DC voltages $V_{RA}$ and $V_{RB}$. The canceling circuit 12 comprises a phase inverter circuit 15 and an adder circuit 16. The inverter circuit 15 reverses the polarity of the output signal from one of the smoothing circuits 10 and 11. The adder circuit 16 produces the sum of the DC voltage $V_{RA}$ whose polarity is reversed by the inverter circuit 15 and the DC voltage $V_{RB}$ whose polarity is not reversed. The canceling circuit 12 can be replaced with a subtractor circuit. The phase inverter circuit 15 is an inverting amplifier having a degree of amplification of 1 and uses an operational amplifier. The adder circuit 16 consists either of an amplifier for applying the changes in both DC voltages to one terminal of said operational amplifier or of a potentiometer for applying the changes in both DC voltages across both ends of the resistor.

Figure 4:
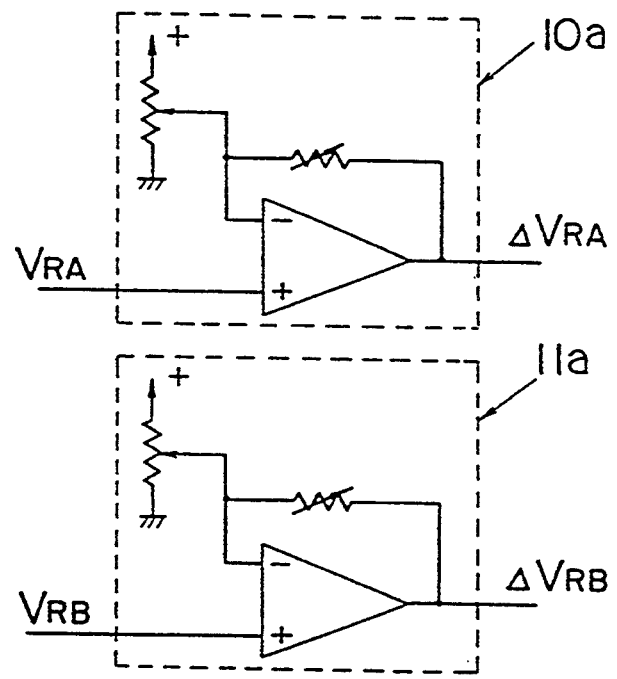
FIG. 4 is a circuit diagram of an average DC voltage-canceling circuit incorporated in the apparatus shown in FIG. 2.

In practice, the DC voltages $V_{RA}$ and $V_{RB}$ are passed through average DC voltage component-removing circuits 10a and 11a (FIG. 4), respectively, before they are applied to the canceling circuit 12 to extract only DC voltage change components $\Delta V_{RA}$ and $\Delta V_{RB}$ due to the flaw 3 or the like. As shown in FIG. 4, these removing circuits 10a and 11a are each composed of an operational amplifier whose cutoff voltage is variable. The output voltage from the adder circuit 16 is amplified to a desired voltage value by the amplifier circuit 13 and delivered as the DC voltage signal $V_0$ from the amplifier circuit 13.

Figure 5:
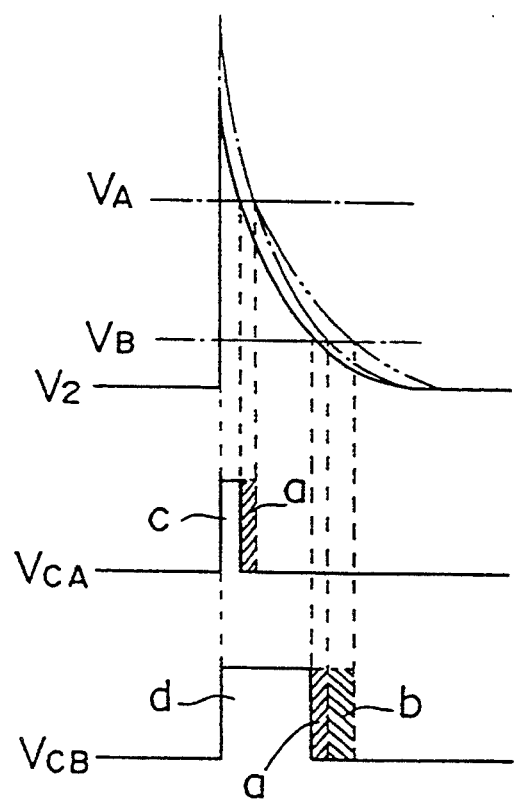
FIG. 5 is a waveform diagram showing main portions of the output voltage from the secondary coil of the apparatus shown in FIG. 2, the main portions being affected by variations in the distance between the sensor and the object and also by flaws.

When the sensor 1 is brought into contact with the surface of the object 2 under inspection as shown in FIG. 1, the voltage pulse $V_2$ having a peak value corresponding to the material of the object 2 is induced in the secondary coil 6. The sensor 1 is moved along the surface. When the sensor passes over the flaw 3 such as a hairline crack or defect, the voltage pulse $V_2$ is affected by the flaw 3. In particular, the eddy currents induced at a normal, or flawless, surface of the object 2 by the primary coil 5 are attenuated by the electrical resistance intrinsic to the material of the surface. However, at the surface having the flaw 3, the attenuation rate varies, and the pulse duration of the voltage pulse $V_2$ is affected. When the sensor 1 is brought close to the object 2, the peak value and the pulse duration of the pulse voltage $V_2$ are varied as a whole according to the kind of material forming the object 2. The effect of the variations in the distance between the sensor and the object is indicated by the dot-and-dash lines in FIG. 5. Generally, when the sensor moves close to a nonferrous material such as aluminum or copper, the peak value and the pulse duration of the pulse voltage $V_2$ tends to decrease. When the sensor approaches ferrous alloys or steels, the peak value and the pulse duration tend to increase. FIG. 5 shows the case in which the sensor 1 is brought close to the object 2 consisting of a ferrous material. The effect of variations in the distance between the sensor and the object on the pulse duration of the voltage pulse $V_2$ differs somewhat between higher and lower voltage portions of the voltage pulse $V_2$, but the effect can be made substantially uniform by making the degree of amplification different between the average DC voltage component-removing circuits 10a and 11a. It is also to be noted that the effect of the flaw 3 indicated by the phantom lines appears only at the trailing portion of the voltage pulse $V_2$. The present invention exploits these features.

As shown in FIG. 5, the pulse duration of the voltage pulse $V_2$ is detected by using the threshold voltages $V_A$ and $V_B$. The threshold voltage $V_A$ is not affected by the flaw 3 but the pulse duration increases or decreases, depending on the distance between the sensor and the object. The threshold voltage $V_B$ is widened or narrowed according to the distance between the sensor and the object and is widened or narrowed by the flaw 3. As a result, the rectangular-wave voltage $V_{CA}$ containing only the component a indicating the distance and the rectangular-wave voltage $V_{CB}$ containing the component b indicating the flaw 3 as well as the component a are produced. Both signals are smoothed and then passed through the canceling circuit 12 to cancel out the component a indicating the distance. The result is that the produced output signal contains only the component 5 indicating the flaw 3. However, this output signal contains a DC voltage component and, therefore, it is necessary to remove this component. More specifically, the rectangular-wave voltages $V_{CA}$ and $V_{CB}$ contain DC voltage components c and d, respectively. Since it is impossible to completely remove these components c and d only by the canceling circuit 12, these components are removed by the average DC voltage component-removing circuits 10a and 11a before applied to the canceling circuit 12. It is also possible to remove the average DC voltage components from the output voltage from the canceling circuit 12.

Figure 6:
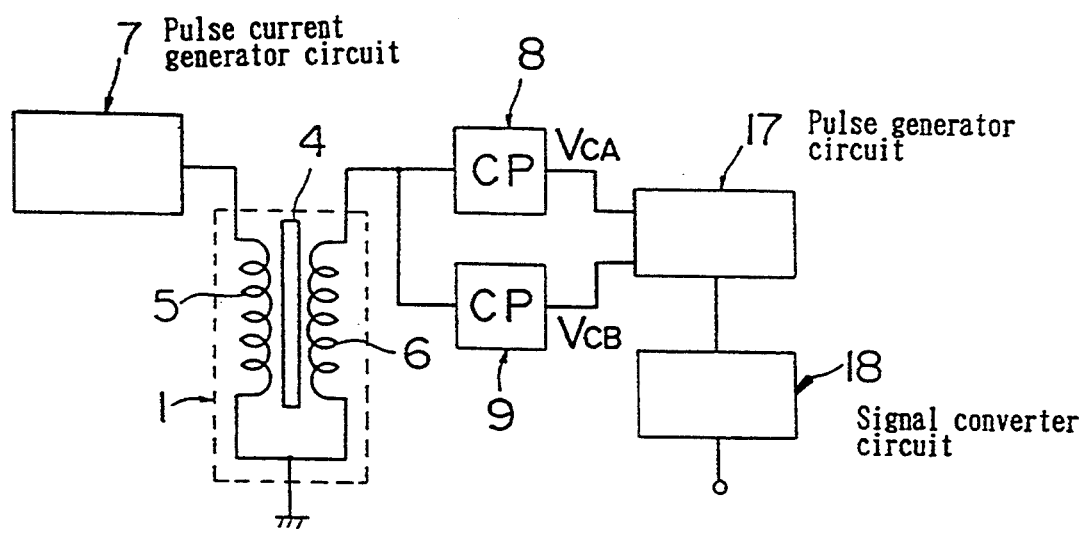
FIG. 6 is a schematic circuit diagram of another eddy current flaw detection apparatus according to the invention.

In the present embodiment, the rectangular-wave voltages $V_{CA}$ and $V_{CB}$ are rectified by the smoothing circuits 10 and 11, respectively. The average DC voltage components are removed by the average DC voltage component-removing circuits 10a and 11a, respectively. Then, the component a indicating the variations in the distance is canceled. This component a can also be removed by a pulse generator circuit 17 and a signal converter circuit 18 shown in FIG. 6. The pulse generator circuit 17 produces a rectangular-wave voltage having a pulse duration equal to the difference between the pulse durations of the rectangular-wave voltages $V_{CA}$ and $V_{CB}$. The signal converter circuit 18 produces a DC voltage signal or digital signal proportional to the pulse duration of the output voltage from the pulse generator circuit 17.

The DC voltage signal $V_0$ shown in FIG. 3 is directly displayed with an analog meter. Alternatively, this signal is converted into a voltage proportional to the voltage by a voltage-frequency converter circuit and then the frequency is counted to provide a digital display. The DC voltage signal $V_0$ may also be used to activate a sound generator or a light-emitting device, for producing sound or light.

When the flaw 3 within the object 2 is detected practice, a pseudo-cracked sample of the same material as the object is prepared, since the effect of variations in the distance between the sensor and the object differs among materials as described above. The threshold voltages $V_A$ and $V_B$ of the comparators are adjusted so that the effect of the variations in the distance between the sensor and the object on the normal, or flawless, surface is minimized. Then, the gains are again adjusted so that the crack in the pseudo-cracked sample surface may be detected with a given sensitivity. Also, a pseudo-cracked sample having a flaw of a known width and a known depth may be used, and adjustments may be adjusted such that the reading of a digital or analog meter is proportional to the depth or other factor.

Figure 7:
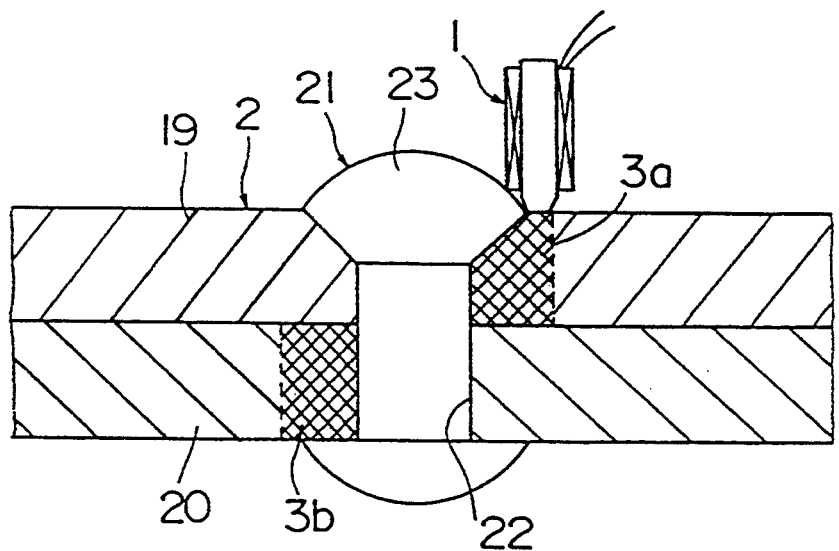
FIG. 7 is a fragmentary cross section of two plates riveted together, for showing the manner in which flaws around the rivet hole are detected by the sensor shown in FIG. 1.

Referring next to FIG. 7, two nonferrous plates 19 and 20 are placed on top of each other and joined together by an aluminum rivet 21 to form an object 2 to be inspected. An eddy current flaw detection apparatus adapted to detect a flaw 3 within this object 2 is next described. For convenience, it is assumed that the plate 19 is located on the other plate 20, and that a flaw 3a such as a hairline crack or defect is formed in the upper plate 19 around a rivet hole 22 into which the rivet 21 is pressed. A flaw 3b is formed in the lower plate 20. In FIG. 7, the flaws 3a and 3b are indicated by cross-hatching.

Figure 8:
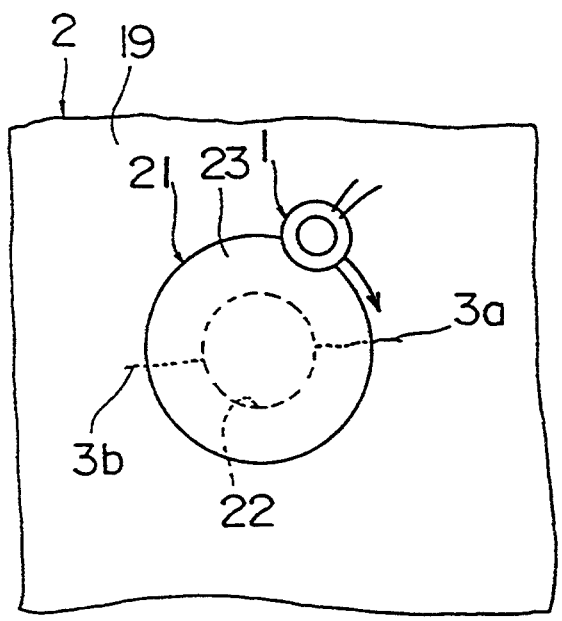
FIG. 8 is a plan view of the two plates and the sensor shown in FIG. 7.
Figure 9:
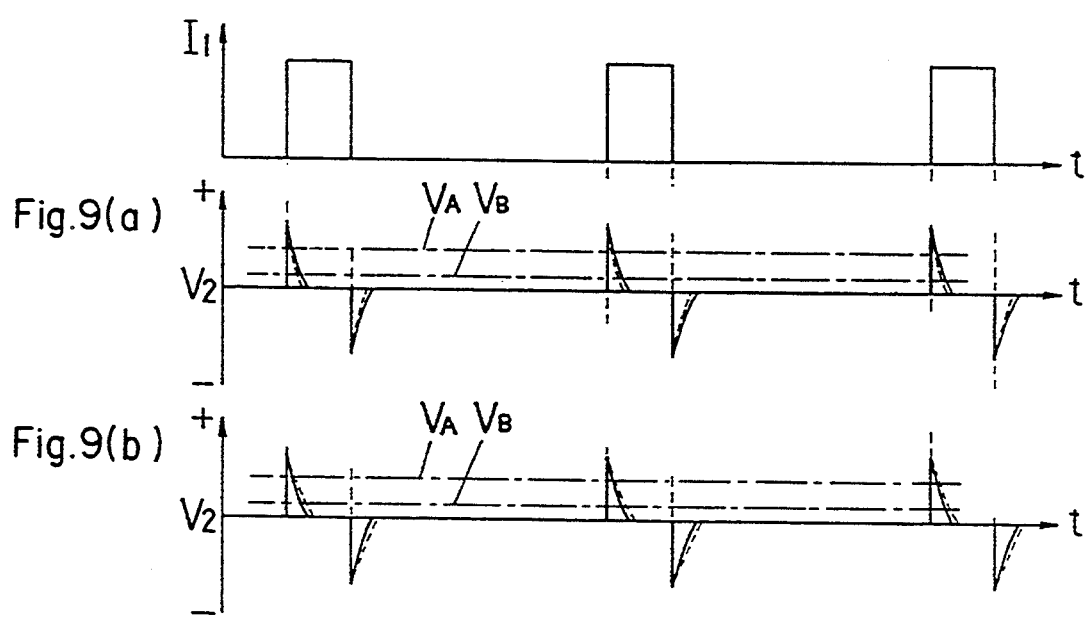
FIGS. 9(a-b) represent a time chart showing the waveforms of signals indicating flaws in the upper and lower plates shown in FIGS. 7 and 8.

As shown in FIG. 8, in order to detect the flaws 3a and 3b, the sensor 1 is caused to scan the surface of the upper plate 19 along the outer periphery of the head 23 of the rivet 21. The voltage pulse $V_2$ is induced in the secondary coil 6. As shown in FIG. 9(a), if the flaw 3a in the upper plate 19 is detected in a positive pulse, then the pulse duration decreases. As shown in FIG. 9(b) if the flaw 3b in the lower plate 20 is detected, the pulse duration increases.

Figure 10:
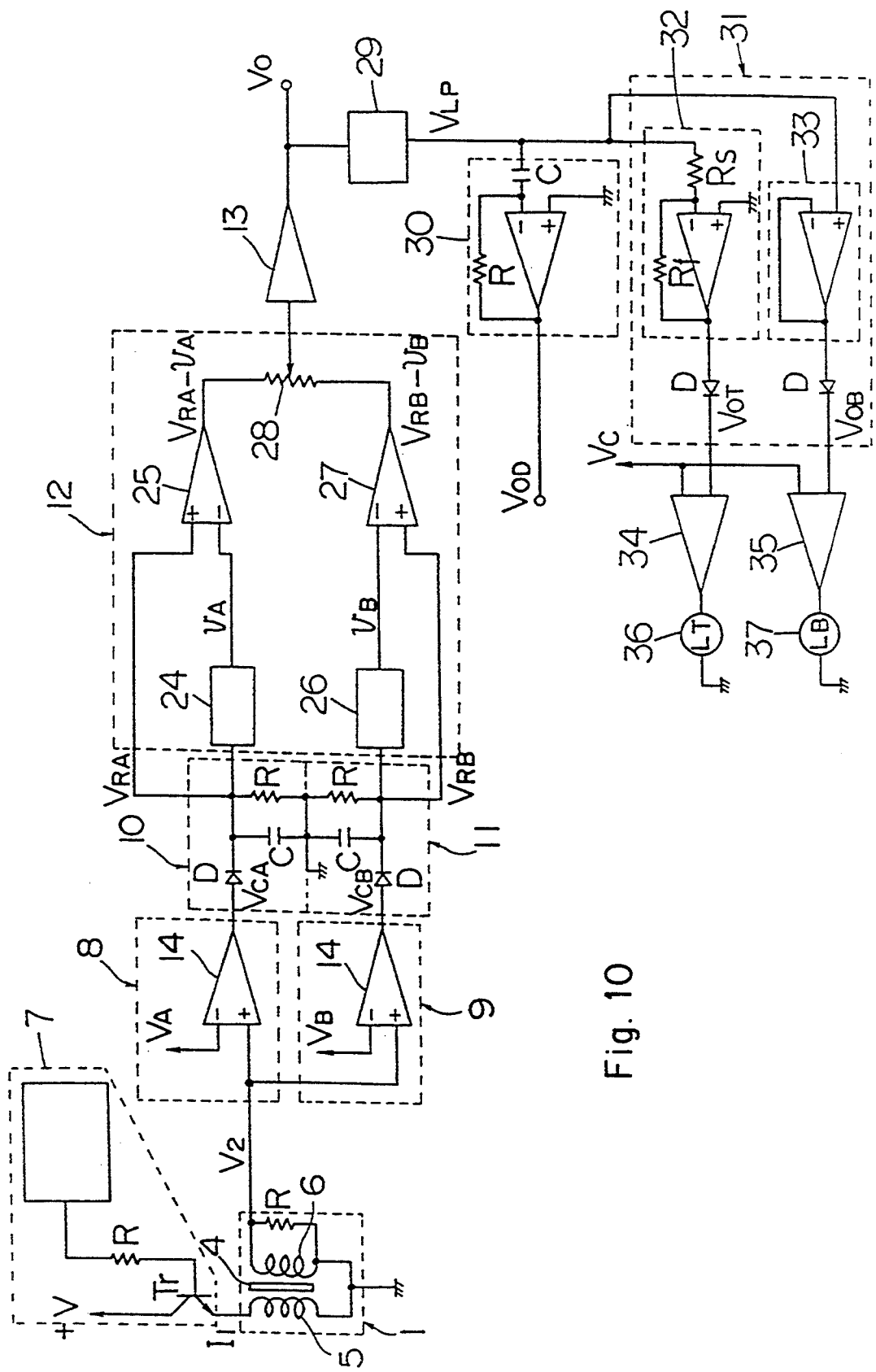
FIG. 10 is a schematic circuit diagram of a further flaw detection apparatus according to the invention.

FIG. 10 is a circuit diagram of this apparatus. The operation of this circuit is next described. It is to be noted that like components are indicated by like reference numerals in various figures and that those components which have been already described in connection FIG. 2 will not be described below. In the canceling circuit 12 of this embodiment, the DC voltage $V_{RA}$ from the smoothing circuit 10 is divided into two, one of which is applied to an analog memory 24, the other being applied to the positive terminal of a differential amplifier 25. The output signal from the analog memory 24 is applied to the negative terminal of the amplifier 25. Similarly, the DC voltage $V_{RB}$ from the smoothing circuit 11 is divided into two. One of them is supplied to an analog memory 26, while the other is furnished to the positive terminal of a differential amplifier 27. The output signal from the memory 26 is applied to the negative terminal of the amplifier 27. The output terminals of the differential amplifiers 25 and 27 are connected to opposite ends of the resistor of a potentiometer 28. The slider of the potentiometer 28 is connected to the amplifier circuit 13.

Figure 11A:
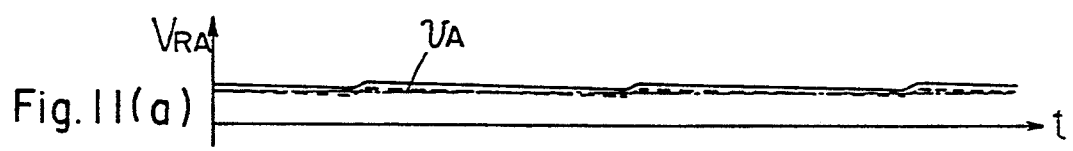
FIGS. 11(a-b) represent a time chart showing the DC output voltages from smoothing circuits incorporated in the apparatus shown in FIG. 10.
Figure 11B:
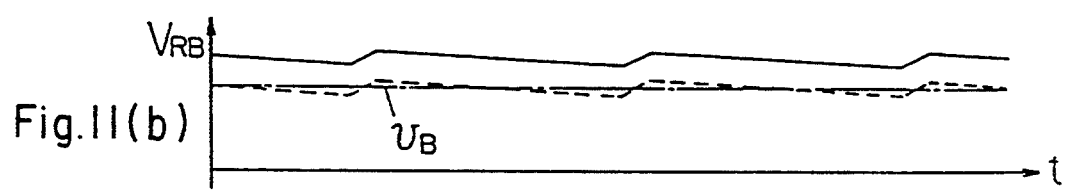

When a given signal is kept applied, e.g., when a set switch is closed, average voltages obtained from the normal, or flawless, portion are stored in the analog memories 24 and 26. When the switch is open, the memories continue to produce the stored voltages. If the apparatus is operated while the sensor 1 is contacted with a normal, or flawless, surface of the object 2, then the DC voltages $V_{RA}$ and $V_{RB}$ from the smoothing circuits 10 and 11 are produced as indicated by the broken lines in FIGS. 11(a-b). Under this condition, the average voltage $V_A$ of the DC voltage $V_{RA}$ and the average voltage $V_B$ of the DC voltage $V_{RB}$ are stored in the analog memories 24 and 26, respectively. The sensor 1 is scanned across the object surface to detect the flaw 3. Then, as indicated by the solid lines in FIGS. 11(a-b), the DC voltages $V_{RA}$ and $V_{RB}$ are generated. The differential amplifiers 25 and 27 produce output voltages $(V_{RA}-V_A)$ and $(V_{RB}-V_B)$, respectively. In response to these output voltages, the potentiometer 28 produces a differential output signal $(V_{RA}-V_A)-(V_{RB}-V_B)$ which is free of the effect of the variations in the distance between the sensor and the object. This differential signal is amplified by the amplifier circuit 13. As a result, the amplifier circuit 13 produces the DC voltage signal $V_0$.

Figure 12A:
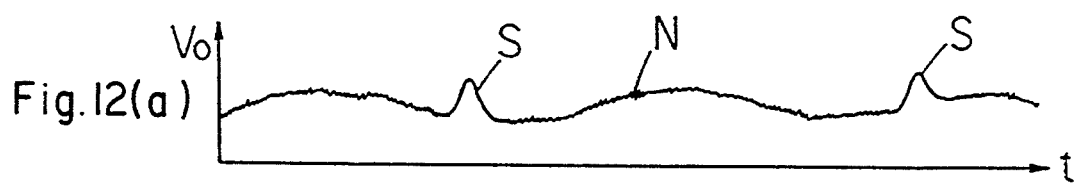
FIGS. 12(a-c) represent a time chart showing a DC voltage signal $V_0$, the output voltage signal $V_{LP}$ from a low-pass filter incorporated in the apparatus shown in FIG. 10, and an output voltage signal $V_{OD}$ from a differentiator.
Figure 12B:
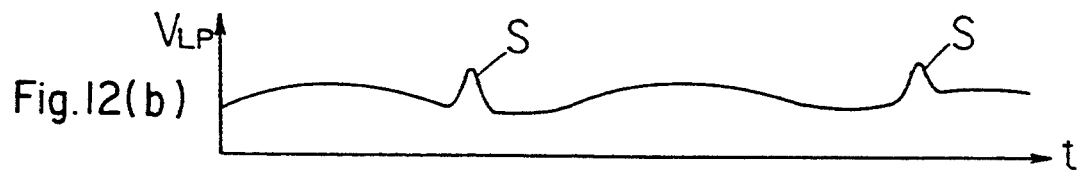
Figure 12C:
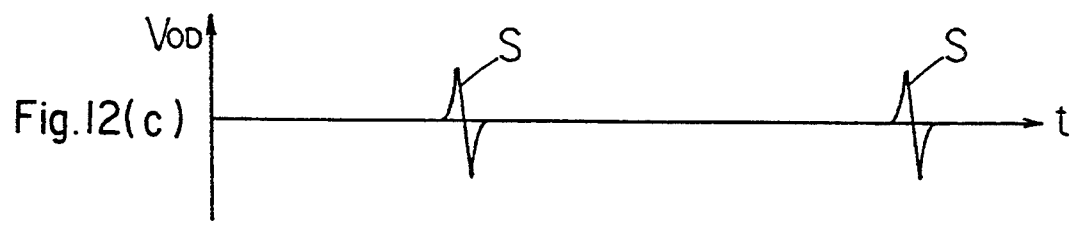

As shown in FIG. 12(a), high-frequency noise N is superimposed on the DC voltage signal $V_0$. In FIGS. 12(a-c), signals indicating a flaw are indicated by S. This noise N can be eliminated, as shown FIG. 12(b) by passing the DC voltage signal $V_0$ through a low-pass filter 29. The voltage signal from the filter 29 is indicated by $V_{LP}$. A wavy component produced by variations in the distance between the sensor 1 and the head 23 of the rivet 21 is also superimposed on the voltage signal $V_{LP}$ when the sensor 1 is scanned along the periphery of the head 23 of the rivet. In the present embodiment, the voltage signal $V_{LP}$ is passed through a differentiator circuit 30 to remove the wavy component, as shown in FIG. 12(c). This differentiator circuit 30 produces an output signal $V_{OD}$.

The presence of a flaw can be detected by monitoring the DC voltage signal $V_0$ or the output voltage signal $V_{OD}$ from the differentiator circuit. However, it is difficult to determine whether this flaw is the flaw 3a in the upper plate 19 or the flaw 3b in the lower plate 20. A signal reflecting the flaw 3a in the upper plate 19 is shown in FIG. 13(a). A signal reflecting the flaw 3b in the lower plate 20 is shown in FIG. 13(b). It can be seen that these two signals swing in opposite directions. Utilizing this, both signals are distinguished from each other by a decision circuit 31 consisting of a surface flaw detection circuit and a deep flaw detection circuit. The surface flaw detection circuit comprises a series combination of an inverting amplifier 32 and a forwardly biased diode D. The deep flaw detection circuit comprises a series combination of a non-inverting amplifier 33 and a forwardly biased diode D. The voltage signal $V_{LP}$ is applied to both amplifiers 32 and 33 and passed through the forwardly biased diodes D. The inverting amplifier 32 produces only a signal $V_{OT}$ indicating a surface flaw, as shown in FIG. 13(a). The non-inverting amplifier 33 produces only a signal $V_{OB}$ indicating a deep flaw, as shown in FIG. 13(d).

These signals $V_{OT}$ and $V_{OB}$ indicating flaws are applied to comparators 34 and 35, respectively, having a threshold voltage $V_C$. When only the signal S indicating a flaw is detected by removing the wavy component, a lamp 36 corresponding to the upper flaw 3a or a lamp 37 corresponding to the lower flaw 3b is lit up.

In the present embodiment, the rivet is made of aluminum. The material of the rivet is not limited to aluminum. The material can also be a nonferrous material. Also in this case, flaws such as hairline cracks and defects around the rivet hole can be detected with high sensitivity.

In the novel eddy current flaw detection method and apparatus described above, a voltage pulse is induced in the secondary coil in response to a rectangular-wave current supplied to the primary coil. The pulse duration of this voltage pulse is detected at two instances in time according to two different voltages. The effect of the variations in the distance between the ferrite core and the conductive object to be inspected is canceled, using both pulse durations. Consequently, the output signal is hardly affected by the variations in the distance. Thus, only signals arising from flaws such as haircracks and defects can be obtained. This greatly improves the accuracy at which flaws are detected.

The voltage pulse induced in the secondary coil is applied to the two comparators having different threshold voltages in detecting the pulse durations of higher and lower portions of the induced pulse voltage. Therefore, if the material of the test object differs, and if the characteristic of the pulse voltage induced in the secondary coil differs, the novel method and apparatus can easily accommodate the different material simply by adjusting the threshold voltages. Hence, the novel method and apparatus can find numerous applications.

Furthermore, the sensor consisting only of a set of coils, i.e., the primary and secondary coils, is employed; a compensating coil may be omitted. Therefore, the signal analysis circuit can be simplified. This leads to a reduction in the cost.

Where two conductive metal plates are placed on top of each other and joined together by a rivet made of a nonferrous metal, flaws such as hairline cracks and defects produced around the rivet hole can be detected with high sensitivity. In addition, it is possible to know whether the detected flaw is located in the upper plate or in the lower plate. That is, deep flaws can be distinguished from surface flaws.

What is claimed is:

1. A method of detecting a flaw within a conductive object to be inspected by eddy current testing, using a ferrite core on which a primary coil and a secondary coil are wound, said method comprising the steps of:

supplying a rectangular-wave current to the primary coil to induce a voltage of a pulse waveform in the secondary coil;

measuring the pulse duration of the induced voltage at two separate time instances corresponding to two different threshold voltages; and canceling the effect of variations in the distance between the ferrite core and the conductive object, using a comparison of the two measured pulse durations, to correctly detect only the flaw.

2. A method of detecting a flaw within a conductive object to be inspected by eddy current testing as set forth in claim 1, wherein (A) the pulse duration of the voltage measured at one of said two separate time instances is measured by the use of a voltage which is affected by variations in the distance between the front end of the ferrite core and the conductive object and which is not affected by the flaw;

(B) the pulse duration of the voltage measured at the other of said two separate time instances, is measured by the use of a voltage which is affected by variations in the distance between the front end of the ferrite core and the conductive object and also by the flaw; and (C) a signal proportional to the difference between these two pulse durations is produced, for correctly detecting only the flaw.

3. An apparatus for performing eddy current testing, comprising:

a sensor having a core on which a primary coil and a secondary coil are wound;

a pulse current generator circuit for supplying a rectangular-wave current to the primary coil which induces a voltage pulse in the secondary coil;

a first comparator connected to said secondary coil which sets a first threshold voltage of the voltage pulse induced in the secondary coil to such a value that the pulse duration of the voltage pulse increases or decreases according to variations in the distance between the front end of the sensor and a conductive object to be inspected but is not affected by a flaw within the object and which produces a rectangular-wave voltage having a pulse duration equal to the amount of time the voltage pulse is greater than the first threshold voltage;

a second comparator connected to said secondary coil which sets a second threshold voltage of the voltage pulse induced in the secondary coil to such a value that the pulse duration of the voltage pulse increases or decreases according to the variations in the distance between the front end of the sensor and the object and is affected by the flaw and which produces a rectangular-wave voltage having a pulse duration equal to the amount of time the voltage pulse is greater than the second threshold voltage;

a first smoothing circuit which smooths the output signal from the first comparator and converts it into a DC voltage proportional to the pulse duration of the rectangular-wave voltage produced from the first comparator;

a second smoothing circuit which smooths the output signal from the second comparator and converts it into a DC voltage proportional to the pulse duration of the rectangular-wave voltage produced from the second comparator; and a canceling circuit which produces the difference between the output voltages from the two smoothing circuits and produces a DC voltage output signal that is not affected by the variations in the distance between the front end of the sensor and the object, whereby only the flaw within the object is correctly detected.

4. An apparatus for performing eddy current testing, comprising:

a sensor having a core on which a primary coil and a secondary coil are wound;

a pulse current generator circuit for supplying a rectangular-wave current to the primary coil which produces a voltage pulse in the secondary coil;

a first comparator connected to said secondary coil which sets a first threshold voltage of the voltage pulse induced in the secondary coil to such a value that the pulse duration of the voltage pulse increases or decreases according to variations in the distance between the front end of the sensor and a conductive object to be inspected but is not affected by a flaw within the object and which produces a rectangular-wave voltage having a pulse duration equal to the amount of time the voltage pulse is greater than the first threshold voltage;

a second comparator connected to said secondary coil which sets a second threshold voltage of the pulse voltage induced in the secondary coil to such a value that the pulse duration increases or decreases according to the variations in the distance between the front end of the sensor and the object and is affected by the flaw and which produces a rectangular-wave voltage having a pulse duration equal to amount of time the voltage pulse is greater than the second threshold voltage;

a pulse generator circuit producing a rectangular-wave voltage having a pulse duration equal to the difference between the pulse durations of the output voltages from the first and second comparators; and a signal converter circuit which produces a DC voltage signal or digital signal proportional to the pulse duration of the output voltage from the pulse generator circuit, whereby only the flaw within the object is correctly detected.

5. An apparatus for performing eddy current testing, comprising:

a sensor having a core on which a primary coil and a secondary coil are wound;

a pulse current generator circuit for supplying a rectangular-wave current to the primary coil which produces a voltage pulse in the secondary coil;

a first comparator connected to said secondary coil which sets a first threshold voltage of the voltage pulse induced in the secondary coil to such a value that the pulse duration of the voltage pulse increases or decreases according to variations in the distance between the front end of the sensor and a conductive object to be inspected but is not affected by a flaw within the object and which produces a rectangular-wave voltage having a pulse duration equal to the amount of time the voltage pulse is greater than the first threshold voltage;

a second comparator connected to said secondary coil which sets a second threshold voltage of the pulse voltage induced in the secondary coil to such a value that the pulse duration of the pulse voltage increases or decreases according to the variations in the distance between the front end of the sensor and the object and is affected by the flaw and which produces a rectangular-wave voltage having a pulse duration equal to amount of time the voltage pulse is greater than the second threshold voltage;

a first smoothing circuit which smooths the output signal from the first comparator and converts it into a DC voltage proportional to the pulse duration of the rectangular-wave voltage produced from the first comparator;

a second smoothing circuit which smooths the output signal from the second comparator and converts it into a DC voltage proportional to the pulse duration of the rectangular-wave voltage produced from the second comparator; and a canceling circuit which comprises a first differential amplifier, a second differential amplifier, and a potentiometer having a resistor and divides the output voltage from each of the smoothing circuits into two portions, the outputs of the first and second differential amplifiers being connected across opposite ends of the resistor of the potentiometer, one input terminal of the first differential amplifier receiving directly one portion of the DC voltage from the first smoothing circuit, the other terminal of the first differential amplifier receiving the other portion via a first analog memory, one input terminal of the second differential amplifier receiving directly one portion of the DC voltage from the second smoothing circuit, the other terminal of the second differential amplifier receiving the other portion via a second analog memory, each analog memory acting to store its input voltage and to deliver the stored voltage, the canceling circuit producing a DC voltage signal from the slider of the potentiometer, whereby only the flaw within the object is correctly detected.

6. An apparatus for performing eddy current testing as set forth in claim 5, further comprising: a low-pass filter for removing high-frequency noise superimposed on the DC voltage signal delivered from the canceling circuit; and a differentiator circuit which removes a low-frequency component superimposed on the DC voltage signal and clearly detects only a signal indicating the flaw.

7. An apparatus for performing eddy current testing as set forth in claim 5, further comprising: a low-pass filter for removing high-frequency noise superimposed on the DC voltage signal delivered from the canceling circuit; and a decision circuit which discriminates between a surface flaw within the object and a deep flaw and produces signals indicating the flaws to different terminals.

8. An apparatus for performing eddy current testing as set forth in claim 7, wherein said decision circuit comprises: a surface flaw detection circuit consisting of a series combination of an inverting amplifier and a forwardly biased diode; and a deep flaw detection circuit consisting of a series combination of a non-inverting amplifier and a forwardly biased diode.

9. An apparatus for performing eddy current testing as set forth in claim 7, further comprising a pair of comparators which are connected with opposite output terminals of the decision circuit and produce only signals indicating flaws, the comparators having threshold voltages capable of removing a low-frequency component.

10. An apparatus for performing eddy current testing as set forth in claim 7, further comprising: a pair of comparators which are connected with opposite output terminals of the decision circuit, have threshold voltages capable of removing a low-frequency component, and produce only signals indicating flaws; and a pair of lamps emitting light when the signals indicating flaws are produced.

* * * * *